United States Patent [19]

Das

[11] 4,365,957
[45] Dec. 28, 1982

[54] DUAL PURPOSE PERIODONTAL SURGICAL INSTRUMENT

[76] Inventor: Asha Das, 113-16 76th Rd., Forest Hills, N.Y. 11375

[21] Appl. No.: 274,539

[22] Filed: Jun. 17, 1981

[51] Int. Cl.$^3$ ............................................. A61C 3/02
[52] U.S. Cl. .................................... 433/144; 128/304
[58] Field of Search ............... 433/144, 145; 128/304, 128/305; 30/26, 27, 168, 28

[56] References Cited

U.S. PATENT DOCUMENTS

| | | | |
|---|---|---|---|
| 1,109,924 | 9/1914 | Hoffman et al. | 433/146 |
| 2,960,767 | 11/1960 | Vonhoff et al. | 30/168 |
| 3,203,433 | 8/1965 | Miller | 30/26 |

Primary Examiner—Robert Peshock
Attorney, Agent, or Firm—Sidney W. Russell; Kimbley L. Muller

[57] ABSTRACT

A perio-dontal surgical instrument is disclosed which includes a handle, shank and a cutting head. The cutting head possesses two interior surgical blades each possessing terminus points having their confluence at a substantial V-shape to form an apex. At least one exterior surgical blade is positioned on the cutting head with its beginning at a first point substantially equal to the terminus of one of the adjacent blades. A method of use is also described for this perio-dontal surgical instrument for Gingivectomy and Gingivoplasty operations.

11 Claims, 8 Drawing Figures

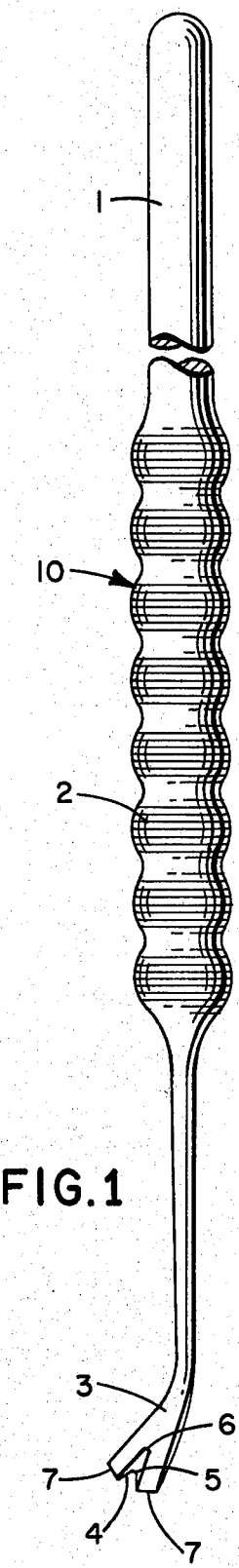
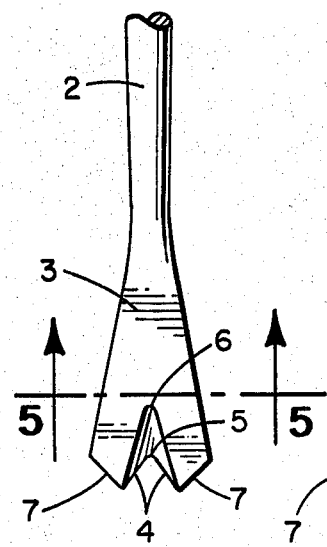
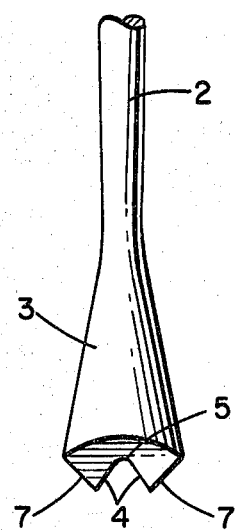
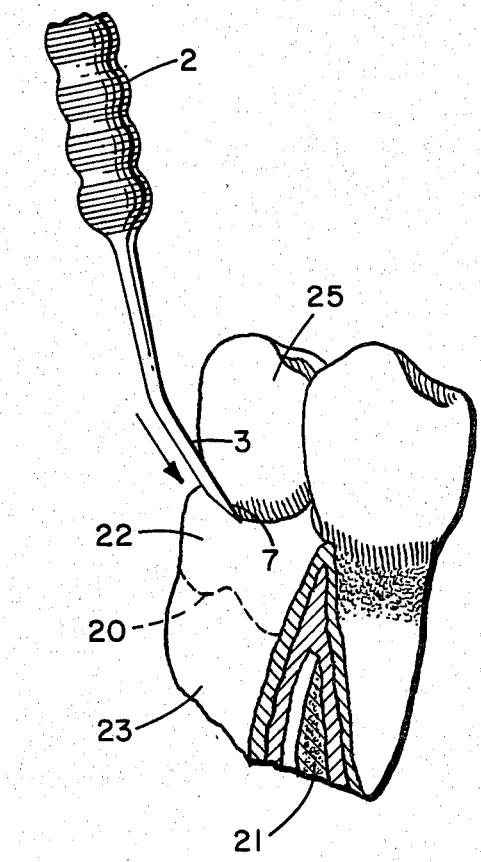

DUAL PURPOSE PERIODONTAL SURGICAL INSTRUMENT

BACKGROUND OF THE INVENTION

Perio-dontal surgery has acquired the status as a viable technique in order to eliminate gum disease and to thereby minimize the premature decay of gums and teeth. However, a great number of dental practioners still fail or at least shy away from performance of such intricate surgery as a result of not only their lack of knowledge of adequate techniques but also as a result of the complications which can arise utilizing various presently known perio-dontal surgical instruments such as a Kirkland Knife or Smith Curet. These latter two instruments form an open-ended blade to cut the gums or diseased gingiva in order to get at or remove diseased gums or a portion of the alveolar bone. These open ended blades present a safety hazard in that blood vessels, nerves, cheeks or tongue may easily be accidently or inadvertently severed during their use. Also these instruments do not provide an easy access to difficult areas of the mouth such as lingual of upper anterior teeth or distal of posterior teeth. The instant invention provides a new perio-dontal surgical instrument which allows easy manipulation and accessibility to all teeth in the mouth without running the risk of inadvertently severing blood vessels, etc. The instant invention also provides a surgical technique wherein no open ended blade need be placed within the mouth of the patient and thus provides much less anxiety to the usually pusillanimous subject of the surgery. Previous perio-dontal techniques have required even those of extreme superior skill in the surgical techniques to continually insert, maneuver and remove instruments such as the Kirkland Knife or a Scalpel from the patient's mouth. In contradistinction, the instant application provides a dual purpose or even a multi-purpose surgical instrument which can perform more than a single function during even the most complex perio-dontal surgical operations. For instance, the "closed-ended blades" of this perio-dontal surgical apparatus, hereinafter described in more detail, can be used to cut the gingiva or gum during a Gingivectomy, Gingivoplasty (shaping the gingiva to attain physiological gingival contours) or for Osteoplasty or the scraping of dead or diseased material from the tooth itself. It is also contemplated that this instrument may also be used in Root-Planning and Osseous Recontouring.

In order to eliminate some of the problems of the previous perio-dontal surgical techniques, some practioner's have even resorted to electrosurgery for the destruction and removal of diseased tissues. This, however, requires very sophisticated instrumentation and also can result in problems of increased healing time once the perio-dontal surgical pack is removed from the place of incision. Also, electrosurgery is not believed to be as safe a surgical technique (i.e., the bone may be touched) as can be accomplished with the instant perio-dontal surgical instrument.

DISCUSSION OF THE PRIOR ART

A review of applicable dental surgical instruments can be accomplished by review of the compendium of knowledge within U.S. Patent Office Class 433, most particularly subclasses 141 and 144. In 1914, the Patent Office issued a patent to Hoffman et al., 1,109,924, for a dental lancet. The drawings depicted therein show a blade having a crescent-shaped front elevation which is transversely curved so that the terminals of the blade are always directed rearwards, i.e., towards the shank. The cutting edge of the blade is contained within the concave recess of the beforementioned crescent shape. With this blade configuration the gum may be cut along both sides of the tooth as well as posterior to the tooth. Another dental lancet is discussed in a patent issued to Ziesel, U.S. Pat. No. 1,455,374, May 1923. Pockets of pyorrhea alveolaris can be readily removed with this open-ended knife blade. The sides are depicted as being both flat and concavial. The double-edged blades all taper to a flat point leaving the dentist with the decision as to which type of blade angle will permit best access to the gums which need to be cut. Thus, this type of instrument possesses at least all of the hazards of the Kirkland Knife now conventionally used in perio-dontal surgery.

In order to bevel the margin of the tooth at the gumline, Diener developed a surgical instrument for which he received U.S. Pat. No. 2,655,726, in October 1953. The blade end is itself beveled to a flat surface which is maintained in the horizontal position in order to place the cutting edge on the margin in the proper cutting position. Thus, the flat edge acts as a guide to acquire the proper beveled cut of the gumline. Two blades, one concave and one convex are disclosed on the same dental surgical instrument patent issued to Montelius, U.S. Pat. No. 2,366,671 in June 1945. A single edged surgical blade is disclosed in Sholberg, U.S. Pat. No. 3,325,900 in attachment with a blade holder having an attachable pivot and a shank. Thus, any configuration of open-ended blades can be attached to the angular shank.

Surgical knives useful in the general practice of surgical medicine are disclosed in patents usually classified in Class 128, subclasses 305, 305.5, 314 and 303. An instrument for cutting the soft wrappings of a plaster case is disclosed in a 1968 patent issued to Cunningham, U.S. Pat. No. 3,365,798. This device possesses interior adjacent blades to cut the soft wrappings without binding or bunching the same between the adjacent edges. An inclined angle is provided at the terminus of one of the adjacent blades in order to remove the cut bandages as they ride up the inclined surface of the cutting utensil. This device is also disclosed to be used only in conjunct association with a circular saw normally required to break up the exterior portion of a plaster case so that the soft wrappings may be severed, which will remove completely the leg, arm, etc. from the case. Another surgical knife is disclosed in U.S. Pat. No. 3,221,744 issued to Stryker in which a recess blade is held between two perpendicular outstanding probes. The blade is depicted as one which can easily and quickly be removed from the handle or shank structure to reduce the cost of surgical instruments while not affecting the curring condition of the blade. A surgical knife useful for cutting through bone material without burring or becoming deformed as its cutting point is disclosed in a patent issued to Krutz in January 1972, U.S. Pat. No. 3,636,955. This blade comprises two planar surfaces which met at a cutting edge. A third planar surface is provided at an angle other than 90° at the tip of the blade. This tip forms a cutting edge which is used to cut new tissue adjacent to the edge formed by the intersection of the two planar surfaces. Another dual bladed surgical instrument is disclosed in Gibbs, U.S. Pat. No. 3,990,451, November 1976. As shown in FIG. 3 of that patent, cutting edges 28 and 30 are provided in a concave navicular-shaped opening with the cutting edges outwardly convex in a direction away from the handle. This instrument is taught as being a general surgical instrument but may be utilized against lesions in the mouth at angles of 30° to 60° depending upon the plane of the minor axis of navicular opening.

Different types of cutlery are classified in Class 30, subclasses 26, 27, 28, 29, 134, 169, 172 and 289. A nailcutter patent issued in 1888 as U.S. Pat. No. 385,914 discloses a V-shaped knotch at the extremity of a knife with beveled edges. Another manicuring instrument is disclosed in U.S. Pat. No. 2,918,924 issued to Pesko wherein cutting edges are situated in a direction away from the handle with wings forming a V-shaped manicuring area therebetween. In 1924 a U.S. patent issued to Kracht, U.S. Pat. No. 1,489,603 for a corn cutter utensil. The cutting edges in that disclosure are concave with respect to one another and meet in a blunt semi-circular edge. A channeling and edging tool is disclosed in U.S. Pat. No. 137,404 having a V-shaped opening converging at the apex of the cutting edges. This type of tool is useful in the edging of leather goods for harness makers, saddle users or probably even leather belts. A kitchen utensil for peeling fruits and vegetables having a substantially concave bottom surface is disclosed in U.S. Pat. No. 3,978,583 issued to Papalardo. The edges of the cutting section of this utensil are concave and sharpened downwardly in order to provide a better peeling technique as demonstrated in FIG. 7 of that patent. Finally, another manicuring implement is disclosed in Lovette, U.S. Pat. No. 1,855,063, having a recessed portion receptive to the end of a finger nail. The prior art has failed to acknowledge the structure of this surgical instrument or the advantages derived from the use of the same in the mouth of the patient.

In one embodiment this invention relates to a surgical instrument which comprises a handle, a shank and a cutting head, wherein said cutting head comprises at least three surgical cutting blades inclusive of: (a) two interior surgical cutting blades each possessing terminus points at one end of said blades and forming a V-shaped apex at the confluence of the end opposite to the ends of said terminus points; and (b) at least one exterior surgical blade having a first end initiating at the terminus point of one of said interior blades and having a terminus point in a straight line with respect to said first end.

Another embodiment of this invention relates to the aforementioned surgical instrument wherein the head includes four (4) surgical cutting blades, two interior joined at their confluence in the apex of a V-shape and two exterior initiating at the end opposite the apex and extending in a straight line, i.e.,  .

Yet another embodiment of this invention resides in a head of a surgical instrument which comprises two interior adjacent blades forming a concavial confluence at the terminus thereof and at least one exterior surgical blade having its beginning at the end opposite confluence of one of said interior adjacent blades and its other end at another point on the surgical head.

Another embodiment of this invention resides in such a surgical instrument head wherein the interior adjacent blades are of uneven length, i.e.,  or  .

Another embodiment of this invention resides in a surgical head wherein said confluence of interior blades is in the curved shape, i.e.,  or  .

Another embodiment of this invention resides in a surgical head wherein the angle of confluence at the apex ranges from 10° to 120°.

DESCRIPTION OF INVENTION

Gingivectomy and Gingivoplasty are both scientific and artist periodontal surgical techniques presently performed with an open-ended blade hand-held instrument. In order to eliminate various problems incurred during the performance of Gingivectomy and Gingivoplasty, a new one-step surgical instrument has been developed as hereinafter defined. Added dental uses in addition to the Gingivectomy and Gingivolplasty are Root Planning and Epithelial Cursettage.

The instrument is made of a conventional metal such as a very high quality steel; for example, a chromium steel or stainless steel which will not rust easily during cold sterilization or use in the mouth. The instrument should not need continual sharpening as in the case of an open-ended blade. It is contemplated that metal is the preferred material of construction although other materials such as very hard plastic or rubber may be utilized where it is deemed necessary, especially in the shank or handle of the instrument. Two of the actual cutting blades of this instrument are adjacent to one another and at least one other blade (preferably two) is positioned in interconnection therewith. These cutting edges are preferably tapered to cut not only soft gingiva tissue, but also hard surfaces like teeth or bone. It is also contemplated that the shank, shaft or handle may be of any configuration so as to fit the surgeons hands without becoming bothersome or cumbersome. It is preferred that the shaft be of a smooth structure while the shank is made of a undulated metal configuration having a pattern stamped on the surface. The novelty of this invention resides in the configuration of the blades on the cutting head of the surgical instrument. It is also contemplated that a replaceable and disposable shaft or shank may be utilized and attached to the cutting edge at any angle for access to various hard to reach areas of the mouth. The instant apparatus will allow both the removal of diseased gum material after the correct pocket marker and a scallop cut have been performed to remove the same.

The instrument is held with a normal pen-grip resting on the third finger. The instrument is capable of trimming off a various yet exact amount of tissue until all of the diseased gum or tooth is removed, however, it is preferred that up to about 1 to about 2 mm of the gingiva may be removed in one piece with great ease leaving a contoured gingival margin.

This instrument may be used for any applicable dental or surgical technique but its preferred method of use is for Gingivectomy, Gingivoplasty, Osseous Recontouring or Root Planning. It is normal procedure in doing a Gingivectomy or Gingivoplasty that a conventional pocket marker is utilized to indicate to the dentist or surgeon the depth of gum disease. After this situs on the side of the gums is adequately marked, the instant instrument is utilized with the blade portion positioned on the exterior of the cutting head (depicted as numbers 7 in FIG. 2) to cut at an angle substantially parallel to the plane of the tooth. The instrument is inserted downwardly between the diseased gum and the tooth allowing the aforementioned exterior cutting edge to separate the diseased gum from the tooth in a downward cutting motion. This motion should be continuous and provide a cut at least as deep as the indicated pocket marker on the outside of the patient's gingiva. This cut may be perfected on either side of the tooth or on both sides of the tooth and in either the front or back of the patient's mouth. After this severing cut, the gum material is loosened from its normal attachment with the tooth. Subsequently, it is necessary to perform a cut substantially perpendicular to the tooth using the adjacent closed-ended blades (depicted as numbers 4 in FIG. 2). It should be noted that these blades are shown herein containing nearly equal adjacent cutting edges. However, it is contemplated within the scope of this invention that these cutting edges may be joined at varying or differing angles so as to provide a longer cutting edge on one adjacent surface than on the other. In this latter embodiment the angle at the apex will change but should be maintained in the range from a very narrow angle of 10° to an angle as wide as 120°. These blades which meet at the apex (number 5 of FIG. 2) are utilized to perform a scalloped-type cut perpendicular to the tooth. This cut may be performed by either or both of the adjacent edges or the cut can be inflicted by the blade at the confluence of the two edges (i.e., the apex). It is preferred that the cut be made in one continuous motion perpendicular to the tooth, however, many such cuts may be utilized to perform or obtain a serrated cutting section of the gum. Subsequent to this cutting, gingiva tissue can now easily be removed from its juxtaposition with the tooth. Thus, the only remaining gum is that which was indicated to be below the pocket marker on the bottom teeth or above the pocket marker on the upper teeth, that is, only healthy gums are allowed to surround the teeth and hence prevent any further spread of the gum rot to other areas of the mouth.

Subsequent to the removal of the gingiva tissue the instrument may be utilized to remove portions of diseased bone or to recontour bone in any manner. The diseased portion of any bone in the mouth will normally not be as brittle or as hard as the healthy portion. It can readily be visualized that the instant adjacent cutting blade may be utilized to scrap or cut the diseased bone material away from the healthy tooth or bone. Thus, at the end of the operation only healthy gingiva tissue and healthy alveolar bone remains in juxtaposition to a healthy tooth. For aesthetic purposes, the instrument may be utilized to plane the surface of the tooth without running the risk of cutting the same too deeply. The back edge of the cutting head is contoured to form a smooth surface and the apex of the blades is beveled rearwardly to avoid any sharp edge on the back or bottom of the cutting head.

BRIEF DESCRIPTION OF DRAWINGS

FIG. 1 is a pictorial view of a complete unitary surgical instrument with cutting head, shank and handle.

FIG. 2 is a front elevational view of the cutting head of the instrument.

FIG. 3 is a side elevational view of the cutting head.

FIG. 4 is a rear elevational view of the cutting head.

FIG. 5 is a cross-section taken along the line 5—5 of FIG. 2.

FIGS. 6, 7 and 8 show the instant apparatus and the technique of its use in order to remove diseased gums or gingiva tissue.

DETAILED DESCRIPTION OF THE DRAWINGS

Figure 7:
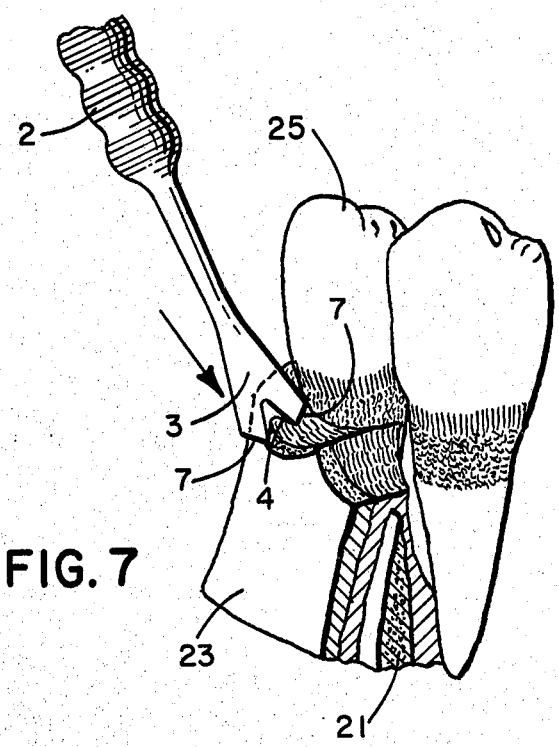

FIG. 1 shows the instant surgical apparatus 10 having a handle 1, a shank portion 2 and a surgical blade head portion 3. It is contemplated within the scope of this invention that any conventional handle 1 or shank 2 may be utilized and attached either permanently or tentatively to the blade head portion 3. It is also preferred within the scope of this invention that the shaft portion be tapered with the upper portion of the same having an undulated or serpentine configuration. The shaft portion may also have a turned-metal or perforated outer surface in order to aid the grip of the surgeon.

The novel aspect of this invention resides in the location of the cutting blades on the head in relation to one another. In FIG. 2, these cutting blades are shown at the end of the instrument as two adjacent closed-end blades 4 meeting at an apex 5, which itself may be tapered to an unsharpened point 6. These adjacent blades and the apex are of extremely sharp makeup and can be utilized to perform the scallop cut during periodontal surgery. The point at the apex 5 is also very sharp and can be used in the scrapping of teeth or gums as the surgical situation warrants. The second set of surgical blades situated on the cutting edge are positioned at the extremity of the instrument and are juxtaposed to the beginning terminus of the adjacent blades, i.e., away from the apex. These exterior blades are denoted as 7. The underside portion of the instrument as shown in FIG. 4 is of smooth configuration beveling off at 5. FIG. 5 shows a cross-sectional view of the cutting head of this instrument above the apex 6.

Figure 8:
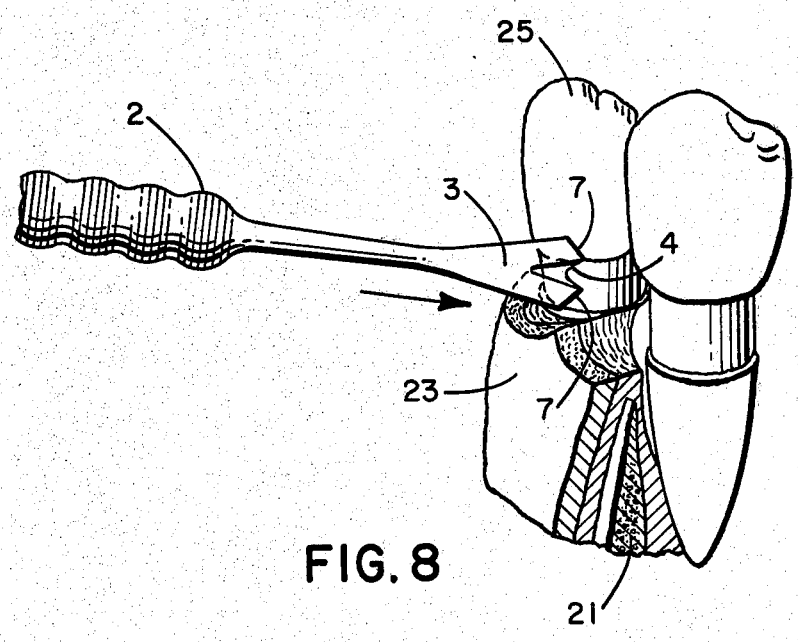

FIGS. 6, 7 and 8 demonstrates the technique of use of the instant apparatus in order to remove diseased gum from a section of a tooth and the recontouring of the same. In FIG. 6, a broken line 20 has been shown to indicate the portion of diseased gums 22. The alveolar bone 21 is shown beneath the diseased portion. The exterior blade 7 is inserted between the tooth 25 and the diseased gum area 22 in order to separate the diseased gum from the underlying section of the tooth. Once this is performed a scallop cut is made as shown in FIG. 7 with the two interior adjacent blades or the apex of the two interior adjacent blades in order to remove completely diseased gum 22 of FIG. 6 from the healthy tissue 23. It should be noted that blades 7 do not perform any substantial cutting in the scallop cut of FIG. 7 nor do the two interior adjacent blades 4 do any substantial cutting when separating the diseased gum from the tooth. FIG. 8 demonstrates the use of the two interior adjacent blades or the apex of the adjacent blades in contouring the portion of the tooth, which will remain exposed subsequent to the periodontal surgery.

It is not contemplated that this invention should be limited to this specific type of periodontal technique but should be applicable to all surgical operations of the mouth where the same can be more readily utilized with this instrument. The technique depicted in FIG. 6 through 8 of this invention is therefore not to be construed as a limitation upon the invention but only as one illustrative embodiment of how to use the instant surgical instrument.

I claim as my invention:

1. A surgical instrument which comprises a handle, a shank and a cutting head, wherein said cutting head comprises at least three surgical cutting blades inclusive of:
   (a) two interior surgical cutting blades each possessing terminus points at one end of said blades and forming a V-shaped apex at the confluence of the end opposite of the ends of said terminus points; and (b) at least one exterior surgical blade having a first end initiating at the terminus point of one of said interior blades and having a terminus point in a straight line with respect to said first end.

2. The surgical instrument of claim 1 wherein each of said interior surgical cutting blades possesses varying lengths measured from their confluence to their terminus point.

3. The surgical instrument of claim 1 wherein said cutting head possesses two exterior surgical blades each having a first end initiating at a first point substantially equal to said terminus of said interior surgical blades and each extending to a second point of said surgical head in a straight line from said first point.

4. The surgical instrument of claim 3 wherein said exterior baldes are of uneven length.

5. The surgical instrument of claim 1 wherein said apex at the confluence of said interior surgical blades forms an apex surgical point.

6. The surgical instrument of claim 1 or 2 wherein the apex of his cutting head is tapered to a plane even with the planar surface of the cutting head.

7. A head of a surgical instrument which comprises two interior adjacent blades forming a concavial confluence at the terminus thereof and at least one exterior surgical blade having its beginning at the end opposite confluence of one of said interior adjacent blades and its other end at another point on the surgical head.

8. The surgical instrument head of claim 7 wherein said concavial confluence forms an apex of a V-shape.

9. The surgical instrument head of claim 8 wherein the adjacent blades of said V are of unequal length.

10. The surgical instrument head of claim 1 or 8 wherein the angle of the apex intersection of the two interior adjacent blades ranges from about 10° to about 120°.

11. The surgical instrument of claim 1 wherein said exterior surgical blade is utilized to make an incision between a patient's diseased gum and tooth in a plane substantially parallel to said tooth and wherein said two interior surgical blades or the apex formed from their confluence is utilized to cut the patient's gum at a point substantially equal to the depth of said first cut with said exterior surgical blade and perpendicular to the tooth of the patient.

* * * * *